(12) United States Patent
Vilsmeier

(10) Patent No.: US 6,714,629 B2
(45) Date of Patent: Mar. 30, 2004

(54) METHOD FOR REGISTERING A PATIENT DATA SET OBTAINED BY AN IMAGING PROCESS IN NAVIGATION-SUPPORTED SURGICAL OPERATIONS BY MEANS OF AN X-RAY IMAGE ASSIGNMENT

(75) Inventor: Stefan Vilsmeier, Kufstein (AT)

(73) Assignee: BrainLAB AG, Heimstetten (DE)

( * ) Notice: Subject to any disclaimer, the term of this patent is extended or adjusted under 35 U.S.C. 154(b) by 31 days.

(21) Appl. No.: 09/851,359

(22) Filed: May 8, 2001

(65) Prior Publication Data

US 2002/0031204 A1 Mar. 14, 2002

(30) Foreign Application Priority Data

May 9, 2000 (EP) .............................. 00109193

(51) Int. Cl.$^7$ ................................ A61B 6/00
(52) U.S. Cl. ..................... 378/165; 378/20; 378/94; 378/210; 600/425
(58) Field of Search ............... 378/20, 94, 98, 378/98.2, 98.5, 165, 210; 600/411, 415, 420, 425, 426, 427

(56) References Cited

U.S. PATENT DOCUMENTS

| | | | | |
|---|---|---|---|---|
| 4,501,009 A | * | 2/1985 | Abele | 378/19 |
| 5,368,030 A | | 11/1994 | Zinreich et al. | 600/414 |
| 5,383,454 A | | 1/1995 | Bucholz | 600/429 |
| 5,636,255 A | | 6/1997 | Ellis | 378/20 |
| 5,800,352 A | * | 9/1998 | Ferre et al. | 600/407 |
| 6,198,794 B1 | * | 3/2001 | Peshkin et al. | 378/42 |
| 6,285,902 B1 | * | 9/2001 | Kienzle et al. | 600/427 |
| 6,381,485 B1 | * | 4/2002 | Hunter et al. | 600/407 |
| 6,584,174 B2 | * | 6/2003 | Schubert et al. | 378/165 |

FOREIGN PATENT DOCUMENTS

| | | |
|---|---|---|
| EP | 0 488 987 A1 | 10/1991 |
| WO | 98/38908 | 9/1998 |

OTHER PUBLICATIONS

Search Report for priority document EP 00109193.3 from European Patent Office.

* cited by examiner

Primary Examiner—David V. Bruce
Assistant Examiner—Therese Barber
(74) Attorney, Agent, or Firm—Renner, Otto, Boisselle & Sklar LLP

(57) ABSTRACT

The invention relates to a method for registering a patient data set obtained by an imaging process in camera navigation-supported surgical operations, comprising the following steps:

producing a patient data set by means of a tomographic scan or an imaging process for the body of the patient or a part thereof, applying at least one marker array, identifiable and trackable in the navigation system, to at least one solid body structure, preferably a bone structure, after the patient has been brought into an operating room and during treatment, in particular after the area to be treated has been exposed, producing one or more x-ray images of the area to be treated by means of an x-ray unit, the spatial position of said images in the navigation system being determined, updating, by means of a computer-assisted assignment, the register of the patient data set with the positional data obtained from the x-ray image, and detecting and re-registering movements or relative movements in the area to be treated by tracking said marker array(s) in the navigation system.

9 Claims, No Drawings

METHOD FOR REGISTERING A PATIENT DATA SET OBTAINED BY AN IMAGING PROCESS IN NAVIGATION-SUPPORTED SURGICAL OPERATIONS BY MEANS OF AN X-RAY IMAGE ASSIGNMENT

BACKGROUND OF THE INVENTION

1. Technical Field

The present invention relates to a method for registering a patient data set obtained by an imaging process in camera navigation-supported surgical operations.

2. Description of Related Art

In recent times, surgical operations are being increasingly performed with the aid of so-called navigation systems, which enable the treating doctor to carry out the operation in an image-assisted manner. Such navigation systems are described, for example, in DE 196 39 615 A1, where a passive reflection referencing system is employed, whereas in U.S. Pat. No. 5,383,454 an instrument positioning system is known which uses active emitting, positional markers.

Such navigation systems are based on scan detection done prior to actual surgery, usually at a location other than the actual operating room and often later in time to patient markers already applied. Even when by such a patient scan, for example, a computer tomograph or MRI tomograph, markers are used which can later also be mapped by the navigation system during treatment, there is no way of preventing inaccuracy in in-situ registering in the operating room resulting from a shift in the markers or due to inaccurate methods of registering.

This is why attempts have been made to enhance the accuracy of registering the momentary position in the operating room by x-ray imaging in situ.

Thus, it has been proposed to perform operations with the aid of continual radiographic mapping, i.e. an x-ray unit with an x-ray source and an image amplifier continually furnishing a radiographic image, output on a display to visually assist the doctor during the operation. However, the disadvantage with this is the high exposure to continual x-ray radiation and, in addition, the only image-assistance which can be provided is relatively inaccurate and usually only two-dimensional.

Known from U.S. Pat. No. 4,791,934 is a CT-assisted, stereotactic surgical system in which several two-dimensional radiographic images are produced by means of a C-bow x-ray unit prior to the operative procedure, which are then superimposed with reconstructed images from the scan data set until the momentary position is established with relatively high accuracy, i.e. the tomographic data set in the navigation system is update-registered.

However, this method, too, still results in inaccuracies since the patient may very well be subjected to further movements during a surgical operation. In this respect, also to be kept into consideration is that some surgical operations necessitate massive manipulations already upon exposing the area to be treated, and that these manipulations may change the location of particular patient structures, and in particular their relative location, by several centimeters, despite all the fixing means employed.

Such shifts cannot be taken into account by the x-ray mapping in accordance with U.S. Pat. No. 4,791,934, which is carried out prior to treatment.

SUMMARY OF THE INVENTION

It is an object of the present invention to provide a method for registering a patient data set which overcomes the aforementioned disadvantages of prior art. In particular, it is the intention to create a possibility of implementing position correct navigation throughout the full duration of the operation.

This object is achieved by a method for registering a patient data set obtained by an imaging process in camera navigation-supported surgical operations comprising the following steps:

- producing a patient data set by means of a tomographic scan or an imaging process for the body of the patient or a part thereof,
- applying at least one marker array, identifiable and trackable in the navigation system, to at least one solid body structure, preferably a bone structure, after the patient has been brought into an operating room and during treatment, in particular after the area to be treated has been exposed,
- producing one or more x-ray images of the area to be treated by means of an x-ray unit, the spatial position of said images in the navigation system being determined,
- updating, by means of a computer-assisted assignment, the register of the patient data set with the positional data obtained from the x-ray image, and
- detecting and re-registering movements or relative movements in the area to be treated by tracking said marker array(s) in the navigation system.

The main advantage of the present invention lies in the possibility of enabling extremely accurate navigation to be implemented, i.e. at any time during the operation. All movements or relative movements in the area to be treated can now be mapped by tracking the movement of one or more solid bone structures to thus permit backtrack computation of the change in position of surrounding areas, for example those of soft body parts, from being able to map the shift in these structures. The data of the patient data set thus continue to be available even when the position of the area to be treated, and in particular the relative position of individual structures in the area to be treated, is no longer the same as upon previous mapping by the imaging process (scan).

The possibility of updating the navigation at any time enables treatment to be performed with enhanced accuracy and thus less invasively, this also reducing the duration of such operations and ensuring continual sterility for the duration of the operation.

Any imaging technique is suitable as the method for producing the patient data set within the scope of the present invention, for example CT, MRI (magnetic nuclear resonance tomograph). PET, SPECT methods and ultrasound scanning. Being able to update the registering of the patient data set at any time in accordance with the invention in principle eliminates complicated registration procedures, for example, individual registering of markers on the patient's skin or on the bone surface by applying a pointer trackable in the navigation system. This thus more or less chronologically separates the production of the patient data set from the operation, i.e. patient scans can now be used which were taken weeks before the actual operation. In addition, any set of scan data can be used, since registering is no longer dependent on markers already applied to the patient at the time of production of the patient data set in the imaging process.

DETAILED DESCRIPTION OF THE PREFERRED EMBODIMENTS

In one preferred embodiment of the method in accordance with the invention, marker arrays are applied to each of the body structures movable relative to each other so that the movements of these structures relative to each other can be mapped. In addition, the image content of the x-ray image(s) can be segmented in a computer-assisted manner and thus individual structures, especially structures movable relative to each other, may be mapped as separate objects and assigned to corresponding objects obtained from the patient data set.

This aforementioned segmenting plays an important role in the scope of treating body parts, where bone structures, which can be very well mapped with the x-ray image, are individually movable relative to each other. This is, for example, the case where bone fractures or single vertebra are involved, but also in the case of otherwise articulated bone joints such as, for example, in the thigh and lower leg. In accordance with the invention, such structures movable relative to each other are discretely mapped as single segments and, upon registration of the patient data set, an adaptation is undertaken so that the information from the data set is again available for the updated relative location of the structures as actually existing. In other words, the information as to the positions of segmented parts movable relative to each other furnishes additional information to the patient data set, which can be evaluated in computation with the aid of a computer to ensure that such a patient data set produced, for example, in a somewhat different relative position of the structures, is able to provide an updated, correct indication of the location of individual body portions during the operation. This not only permits taking into account the relative movements of solid structures as directly mapped, to which the marker arrays are directly secured, it also makes it possible to compute the position of surrounding tissue. This applies not only to changes in the relative position between scanning and the actual point in time of the operation, but also to movements occurring during the operation or caused thereby.

Within the scope of the invention, the marker arrays employed may include actively emitting markers as well as reflective markers, and they are applied, for example, via sterile adapters to bone structures, in particular also to spinous processes.

Segmenting, as mentioned above, as well as arranging and assigning the separate and discrete objects is done preferably automatically in the framework of computer-assisted navigation or updating navigation by means of the x-ray image, for which algorithms are available.

One possibility of update-registering the patient data set within the scope of the method in accordance with the invention involves comparing and compensating x-ray images to digital reconstructed radiograms (DRR's) obtained from the patient data set until a situation is found in which the adapted patient data set coincides with the situation actually established radiographically. Methods of mapping the spatial position of DRR's within a navigation system are known and may find application within the scope of the invention. It is furthermore possible in accordance with the invention to implement updating of the registering of the patient data set by comparing and compensating contours from the x-ray image(s) with surface information furnished by the patient data set.

Finally, a further possibility of registering the patient data set in accordance with the invention involves the use of a C-bow x-ray unit, which can be registered and tracked in the navigation system and which is rotatable around a horizontal axis and comprises an isocentric beam path. Upon producing several images from various angles by such an x-ray unit having an isocentric beam path, the images are defined localized isocentrically, and by establishing the position of the x-ray unit itself, for example by means of navigation markers, the location of the created x-ray images can be mapped and used during registration of the patient data set.

In all the cited cases, the assignment of structures from the patient data set and the x-ray image(s) may be done by means of a three-dimensional image fusion technique via gray value calibration.

The method in accordance with the invention thus renders it possible for the first time to perform updated precise navigation, which is unaffected by movements or relative movements (also caused during the operation) in the area to be treated.

In the foregoing description, preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A method for registering a patient data set obtained by an imaging process in camera navigation-supported surgical operations comprising the following steps:
    producing a patient data set by means of at least one of a tomographic scan and an imaging process for at least part of the body of the patient,
    applying at least one marker array, identifiable and trackable in the navigation system, to at least one solid body structure after the patient has been brought into an operating room,
    producing one or more x-ray images of the area to be treated by means of an x-ray unit, and determining the spatial position of said images in the navigation system,
    updating, by means of a computer-assisted assignment, registration of the patient data set with positional data obtained from the x-ray image, and
    detecting and re-registering movements or relative movements in the area to be treated by tracking said marker array(s) in the navigation system.

2. The method as set forth in claim 1, wherein the producing step includes producing the patient data set by one or more of the following techniques: computer tomography (CT), MRI (magnetic nuclear resonance tomograph), PET, SPECT, and ultrasound scanning.

3. The method as set forth in claim 1, wherein the applying step includes applying respective marker arrays to each of at least two solid body structures movable relative to each other so that the movements of said structures relative to each other can be detected.

4. The method as set forth in claim 1, wherein the updating step includes computer-assisted segmenting the image content of said x-ray image(s) and thus individual structures movable relative to each other are mapped as separate objects or assigned to corresponding objects obtained from said patient data set.

5. The method as set forth in claim 4, wherein at least one of the segmenting and mapping and assigning steps is done automatically.

6. The method as set forth in claim 1, wherein the updating step includes comparing and compensating the x-ray image(s) to digital reconstructed radiograms (DRRs) obtained from said patient data set.

7. The method as set forth in claim 1, wherein the updating step includes comparing and compensating contours from said x-ray image(s) to surface information from said patient data set.

8. The method as set forth in claim 1, wherein the updating step includes using a C-bow x-ray unit, which can be registered and tracked in said navigation system, and which is rotatable around a horizontal axis and provides an isocentric beam path.

9. The method as set forth in claim 1, wherein the updating step includes assigning structures from said patient data set and said x-ray image(s) by means of a three-dimensional image fusion technique via gray value calibration.

* * * * *